United States Patent [19]

Takemoto et al.

[11] Patent Number: 4,550,180

[45] Date of Patent: Oct. 29, 1985

[54] METHOD FOR MANUFACTURE OF N-FORMYLASPARTIC ANHYDRIDE

[75] Inventors: Tadashi Takemoto, Kawasaki; Toyoto Hijiya, Yokosuka; Tetsuo Yamatani, Yokkaichi, all of Japan

[73] Assignee: Ajinomoto Co., Inc., Tokyo, Japan

[21] Appl. No.: 589,685

[22] Filed: Mar. 15, 1984

[30] Foreign Application Priority Data

Mar. 25, 1983 [JP] Japan ................................. 58-50245

[51] Int. Cl.$^4$ ........................................... C07D 307/22
[52] U.S. Cl. ................................................. 549/253
[58] Field of Search ....................................... 549/253

[56] References Cited

U.S. PATENT DOCUMENTS 4,508,912   4/1985   Yamatani et al. ................... 549/253

FOREIGN PATENT DOCUMENTS 51-91210   8/1976   Japan ................................. 549/253

Primary Examiner—Henry R. Jiles
Assistant Examiner—Bernard I. Dentz
Attorney, Agent, or Firm—Oblon, Fisher, Spivak, McClelland & Maier

[57] ABSTRACT

In a method for the manufacture of N-formylaspartic acid anhydride which comprises reacting a mixture of aspartic acid, formic acid and acetic anhydride in the presence of an entraining organic solvent, the improvement comprising adding to the mixture, prior to or during the course of reaction, an oxide, hydroxide, or a salt of a metal. The above compound is used as an intermediate in the manufacture of alpha-L-aspartyl-L-phenylalanine methyl ester which is a sweetening agent.

5 Claims, No Drawings

METHOD FOR MANUFACTURE OF N-FORMYLASPARTIC ANHYDRIDE

This invention relates to a method for the manufacture of N-formylaspartic anhydride from aspartic acid. The aspartic acid as involved herein may be in an optically active form or a racemic form.

The method for producing N-formylaspartic anhydride by causing aspartic acid to be acted upon by formic acid and acetic anhydride has been known to the art (Published Unexamined Japanese Patent Application SHO 46(1971)-1370).

In this reaction, there is generally used excess formic acid. When the N-formylaspartic anhydride is manufactured on a commercial basis, therefore, the excess formic acid must be recovered and reused. Incidentally, the aforementioned reaction upon completion produces acetic acid in a ratio of 2 moles per mole of the acetic anhydride consumed. The recovery of formic acid, therefore, inevitably entails separation of formic acid from an acetic acid-formic acid mixed system. As means for this separation, there are two alternative methods, the method which effects the separation by direct distillation of the mixed system or the method which effects the separation by first adding an organic solvent such as toluene to the mixed system and subjecting the resultant three-component system to distillation. Neither of these methods permits easy separation of pure formic acid. To be more specific, they inevitably suffer inclusion in the separated formic acid of extraneous substance; acetic acid in the former method and acetic acid and the organic solvent such as toluene in the latter method.

In the manufacture of N-formylaspartic anhydride, the known method involves use of pure formic acid. It is not known to have permitted use of formic acid containing acetic acid or acetic acid and an organic solvent such as toluene in any case. The inventors have tried the reaction for the production of N-formylaspartic anhydride by using formic acid containing acetic acid or acetic acid and an organic solvent such as toluene, to learn that the product is obtained in notably lower yields than when the production resorts to use of pure formic acid.

N-formyl-L-aspartic anhydride is used as the raw material for the manufacture of α-L-aspartyl-L-phenylalanine methyl ester which is attracting attention as a sweetening agent. When α-L-aspartyl-L-phenylalanine methyl ester is manufactured on a commercial basis, the portion of L-aspartic acid which has escaped being utilized as the aspartic acid component of the product must be recovered and put to reuse. The inventors have tried the same reaction by using the L-aspartic acid thus recovered, to learn that the product of the reaction is obtained in notably lower yields than when the production resorts to use of commercially avaiable L-aspartic acid.

The inventors, therefore, conducted a diligent study with a view to developing a commercially advantageous method for manufacturing N-formylaspartic anhydride without entailing the drawbacks mentioned above. They have consequently perfected the present invention.

The method of this invention can be employed in the manufacture of N-formylaspartic anhydride by the use of formic acid containing acetic acid or acetic acid and an organic solvent such as toluene, in the manufacture of the same compound by the use of the L-aspartic acid recovered during the process for the production of α-L-aspartyl-L-phenylalanine methyl ester, or in the manufacture of the same compound by the use of both of the raw materials mentioned above. This method enables the compound aimed at to be produced in high yields by additionally using in the reaction system an oxide or a hydroxide of a varying metal or a salt of such a metal with a varying acid.

The amount of acetic anhydride to be used in this invention suffices as long as it accounts for at least 2 moles per mole of aspartic acid. If this amount accounts for a ratio of less than 2 moles, the formylation and the anhydride formation do not thoroughly proceed.

The amount of acetic anhydride has no specific upper limit. If acetic anhydride is used in excess there only results a proportional increase in the amount of excess acetic anhydride to be recovered. Such excess use of acetic anhydride can hardly be called a commercially advantageous means. Thus, the amount is desired to account for a ratio in the range of 2 to 2.5 moles.

The amount of formic acid to be used, calculated as pure formic acid, is desired to account for a ratio falling in the range of 2 to 3 moles per mole of aspartic acid. If formic acid is used in an amount accounting for a ratio exceeding 3 moles, there only results a proportional increase in the amount of excess formic acid to be recovered. Such use of excess formic acid can hardly be called commercially advantageous.

The organic solvent to be contained in formic acid may be of any kind insofar as it is inactive to the reactants and the product of the reaction and it is capable of effectively functioning as an entrainer in the separation of formic acid from the formic acid-acetic acid mixed system by distillation. Typical examples are hydrocarbons such as toluene, xylene, and hexane; halogenated hydrocarbons such as chloroform and ethylene dichloride; esters such as ethyl acetate and methyl propionate, and ketones such as acetone and methylethyl ketone.

The reaction temperature, with a view to curbing possible racemization of the product of the reaction to the fullest extent, is selected generally in the range of not more than 100° C. and not less than $-10°$ C., preferably in the range of not more than 80° C. and not less than 0° C.

Examples of the metal compound to be added to the reaction system are oxides and hydroxides of various metals such as alkali metals including lithium, sodium, and potassium; alkaline earth metals including magnesium and calcium; copper-family elements including copper; zinc-family elements including zinc; boron-family elements including aluminum, and iron-family elements including iron; salts of such various metals with various acids, including carbonates, acetates and other carboxylates, hydrochlorides, hydrobromides, nitrates, phosphates, and sulfates. Although the amount of the metal compound additionally used is not specifically limited, it is confined so as not to affect adversely any step following the process of the reaction. The maximum amount of the metal compound tolerated is variable to some extent depending on the particular kind of compound added. In the case of magnesium acetate as in Example 1, for instance, the amount is such as to account for a ratio of 0.0087 mole per mole of L-aspartic acid, indicating that the metal compound manifests its effect even in such a small amount.

The proper amounts of such compounds which are additionally incorporated in the reaction system of this invention as embodied on a commercial scale can be easily found by any person of ordinary skill in the art by conducting a preliminary experiment of the reaction involved. The addition of such compounds to the reaction system is generally made prior to the start of the reaction of anhydride formation. Optionally, it may be effected during the course of the reaction.

As described above, the method of this invention, in the conversion of aspartic acid through reaction with formic acid and acetic anhydride into N-formylaspartic anhydride, permits N-formyl-L-aspartic anhydride to be produced in high yields even when the formic acid contains acetic acid or acetic acid and an organic solvent such as toluene or even when the aspartic acid recovered during the process for the production of α-L-aspartyl-L-phenylalanine methyl ester is used as the raw material.

EXAMPLE 1

A solution was prepared by adding 21 ml (0.21 mole) of acetic anhydride, 9.8 ml (0.25 mole) of formic acid, 3.3 ml of acetic acid, and 3.3 ml of toluene. The solution was stirred with 13.3 g (0.1 mole) of L-aspartic acid and then 0.187 g ($8.7 \times 10^{-4}$ mole) of magnesium acetate tetrahydrate was added thereto. The mixture was kept at 45° C. for 3.5 hours to effect reaction.

The resultant slurry was stirred with 58 ml of toluene added thereto and cooled with ice for one hour. The mixture formed was subjected to suction filtration. Consequently, there was obtained 13.4 g of N-formyl-L-aspartic anhydride in a crystalline form. The yield was 94.0%. The melting point and the infrared absorption spectrum of this compound agreed with those of the standard sample of L-formyl-L-aspartic anhydride.

Separately, the slurry obtained by repeating the reaction mentioned above was concentrated under a vacuum to expel the solvent. The residue of the distillation was dissolved in 100 ml of methanol. The resultant solution was quantitatively separated by high-speed liquid chromatography into N-formyl-L-aspartic acid-α-methyl ester and N-formyl-L-aspartic acid-β-methyl ester. Since the N-formyl-L-aspartic anhydride reacted with methanol to produce the α and β methyl ester compounds, the yield of the N-formyl-L-aspartic anhydride could be calculated by determining the amounts of these ester compounds.

In the reaction mentioned above, the yield of the N-formyl-L-aspartic anhydride was 98.0%.

EXAMPLE 2

In a mixture consisting of 9.8 ml (0.25 mole) of formic acid and 21 ml (0.21 mole) of acetic anhydride, 14.0 g (0.1 mole) of L-aspartic acid 95% in purity recovered in the process of the production of α-L-aspartyl-L-phenylalanine methyl ester, and 0.187 g ($8.7 \times 10^{-4}$ mole) of magnesium acetate tetrahydrate were stirred at 45° C. for 3.5 hours to effect reaction.

The resultant slurry was concentrated under a vacuum to expel the solvent. The residue of the distillation was dissolved in 100 ml of methanol and the solution consequently obtained was quantitatively analyzed by following the procedure of Example 1.

The yield of N-formyl-L-aspartic anhydride was 97.8%.

Comparative Experiment 1

When the reaction of Example 1 was carried out by omitting the addition of magnesium acetate, the yield of N-formyl-L-aspartic anhydride was only 85.0%.

Comparative Experiment 2

When the reaction of Example 2 was carried out by omitting the addition of magnesium acetate, the yield of N-formyl-L-aspartic anhydride was only 83.8%.

EXAMPLE 3

When the procedure of Example 1 was repeated by using L-aspartic acid 95% in purity recovered in the process for the production of α-L-aspartyl-L-phenylalanine methyl ester, the yield of N-formyl-L-aspartic anhydride was 97.5%.

EXAMPLE 4

When the procedure of Example 1 was repeated by using hexane in the place of toluene, the yield of N-formyl-L-aspartic anhydride was 97.8%.

EXAMPLE 5

When the procedure of Example 1 was repeated by using ethyl acetate in the place of toluene, the yield of N-formyl-L-aspartic an hydride was 98.2%.

EXAMPLES 6-9

The reaction was carried out in the presence of a varying compound indicated in Table 1. The conditions, except those indicated in Table 1, and the procedure were similar to those of Example 1.

TABLE 1

| Example | Compound added | Amount added (g) | Yield of reaction (%) |
|---|---|---|---|
| 6 | K.OCOCH$_3$ | 0.080 | 95.6 |
| 7 | MgCl$_2$.6H$_2$O | 0.177 | 98.2 |
| 8 | Ca(OCOCH$_3$)$_2$.H$_2$O | 0.153 | 98.0 |
| 9 | Zn(OCOCH$_3$)$_2$.2H$_2$O | 0.191 | 98.6 |

EXAMPLES 10-13

The reaction was carried out in the presence of a varying compound indicated in Table 2. The conditions, other than those indicated in Table 2, and the procedure were similar to those of Example 2.

TABLE 2

| Example | Compound added | Amount added (g) | Yield of reaction (%) |
|---|---|---|---|
| 10 | K.OCOCH$_3$ | 0.080 | 96.8 |
| 11 | MgCl$_2$.6H$_2$O | 0.177 | 97.5 |
| 12 | Ca(OCOCH$_3$)$_2$.H$_2$O | 0.153 | 97.8 |
| 13 | Zn(OCOCH$_3$)$_2$.2H$_2$O | 0.191 | 97.3 |

What is claimed is:

1. In a method for the manufacture of N-formylaspartic acid anhydride which comprises reacting a mixture of aspartic acid, formic acid and acetic anhydride in the presence of an entraining organic solvent, an improvement comprising adding to the mixture, prior to or during the course of reaction, an oxide, hydroxide or a salt, or a hydrate thereof, of a metal, selected from the group consisting of sodium, lithium, potassium, magnesium, calcium, copper, zinc, aluminum and iron; wherein said salt is selected from the group consisting of carbonate, acetate, chloride, nitrate, phosphate or sulfate.

2. The method of claim 1 wherein relative to a molar quantity of aspartic acid employed, from 2 to 2.5 equivalents of acetic anhydride are added and from 2 to 3 equivalents of formic acid are added.

3. The method of claim 1 wherein the oxide, hydroxide or salt of a metal is selected from the group consisting of $KOCOCH_3$, $MgCl_2.6H_2O$, $Mg(OCOCH_3)_2.4H_2O$, $Ca(OCOCH_3)_2.H_2O$ and $Zn(OCOCH_3)_2.2H_2O$.

4. The method of claim 1 wherein the mixture is reacted at a temperature of from $-10°$ to $100°$ C.

5. The method of claim 4 wherein the temperature is from $0°$ to $80°$ C.

* * * * *